US011987797B2

United States Patent
Zheng et al.

(10) Patent No.: US 11,987,797 B2
(45) Date of Patent: May 21, 2024

(54) **ATTENUATED STRAIN OF AFRICAN SWINE FEVER VIRUS (ASFV) WITH IPTG-INDUCED DELETION OF *D1133L* GENE AND USE THEREOF**

(71) Applicant: LANZHOU VETERINARY RESEARCH INSTITUTE, CHINESE ACADEMY OF AGRICULTURAL SCIENCES, Lanzhou (CN)

(72) Inventors: Haixue Zheng, Lanzhou (CN); Keshan Zhang, Lanzhou (CN); Ting Zhang, Lanzhou (CN); Tao Feng, Lanzhou (CN); Bo Yang, Lanzhou (CN); Xing Yang, Lanzhou (CN); Xijuan Shi, Lanzhou (CN); Hong Tian, Lanzhou (CN); Yi Ru, Lanzhou (CN); Fan Yang, Lanzhou (CN); Zixiang Zhu, Lanzhou (CN); Jianhong Guo, Lanzhou (CN); Jijun He, Lanzhou (CN); Xiangtao Liu, Lanzhou (CN)

(73) Assignee: LANZHOU VETERINARY RESEARCH INSTITUTE, CHINESE ACADEMY OF AGRICULTURAL SCIENCES, Lanzhou (CN)

( * ) Notice: Subject to any disclaimer, the term of this patent is extended or adjusted under 35 U.S.C. 154(b) by 0 days.

(21) Appl. No.: 18/057,588

(22) Filed: Nov. 21, 2022

(65) Prior Publication Data
US 2023/0295641 A1   Sep. 21, 2023

(30) Foreign Application Priority Data
Mar. 16, 2022 (CN) .......................... 202210258522.6

(51) Int. Cl.
*C12N 15/65* (2006.01)
*C12N 7/00* (2006.01)
*C12N 15/63* (2006.01)

(52) U.S. Cl.
CPC ............... *C12N 15/65* (2013.01); *C12N 7/00* (2013.01); *C12N 15/63* (2013.01); *C12N 2710/12021* (2013.01); *C12N 2710/12022* (2013.01)

(58) Field of Classification Search
CPC .......... C12N 15/65; C12N 7/00; C12N 15/63; C12N 2710/12021; C12N 2710/12022; C12N 2710/12062; C12N 9/14; C12N 15/85; C07K 14/005; Y02A 50/30
See application file for complete search history.

(56) References Cited

U.S. PATENT DOCUMENTS

| 2020/0017881 | A1* | 1/2020 | Xie | ...................... A61K 35/768 |
| 2020/0306360 | A1* | 10/2020 | Nikolin | .................. C07K 14/01 |
| 2022/0193217 | A1* | 6/2022 | Gladue | ..................... C12N 7/00 |

OTHER PUBLICATIONS

Cackett, Gwenny, et al. "The African swine fever virus transcriptome." Journal of virology 94.9 (2020): 10-1128 (Year: 2020).*
Liu (Liu, Yancheng, et al. "An in vivo gene deletion system for determining temporal requirement of bacterial virulence factors." Proceedings of the National Academy of Sciences 105.27 (2008): 9385-9390) (Year: 2008).*

* cited by examiner

*Primary Examiner* — Nancy J Leith
*Assistant Examiner* — Kyle Thomas Rega
(74) *Attorney, Agent, or Firm* — MH2 TECHNOLOGY LAW GROUP LLP

(57) ABSTRACT

The present disclosure belongs to the technical field of biology, and in particular relates to an attenuated strain of African swine fever virus (ASFV) with IPTG-induced deletion of a D1133L gene and use thereof. In the present disclosure, it is firstly found that the D1133L protein of ASFV can inhibit production of IFN-β and downstream cytokines ISG-15 and ISG-56, and can be used as an immunosuppressant with a relatively strong immunosuppressive effect. In addition, the attenuated strain of ASFV with IPTG-induced deletion of the D1133L gene is constructed. Specifically, a screening expression cassette is inserted into a position before the non-structural protein gene D1133L of the ASFV using an *Escherichia coli* lac operator-repressor system, to obtain a recombinant virus. In the presence of the IPTG, the recombinant virus has similar characteristics to a wild-type virus; and in the absence of the IPTG, the expression of the D1133L protein is inhibited.

8 Claims, 7 Drawing Sheets
Specification includes a Sequence Listing.

ATTENUATED STRAIN OF AFRICAN SWINE FEVER VIRUS (ASFV) WITH IPTG-INDUCED DELETION OF D1133L GENE AND USE THEREOF

SEQUENCE LISTING

The instant application contains a Sequence Listing XML which has been submitted electronically in XML format and is hereby incorporated by reference in its entirety. Said XML copy, created on Nov. 20, 2022 is named HLP20220501019-sequence listing.xml and is 41,000 bytes in size.

CROSS REFERENCE TO RELATED APPLICATION

This patent application claims the benefit and priority of Chinese Patent Application No. 202210258522.6, entitled "Attenuated strain of African swine fever virus (ASFV) with IPTG-induced deletion of the D1133L gene and use thereof" filed on Mar. 16, 2022, the disclosure of which is incorporated by reference herein in its entirety as part of the present application.

TECHNICAL FIELD

The present disclosure belongs to the technical field of biology, and in particular relates to an attenuated strain of African swine fever virus (ASFV) with IPTG-induced knockout of the D1133L gene and use thereof.

BACKGROUND ART

African swine fever (ASF) is a fulminating infectious disease of hogs and wild boars caused by an African swine fever virus (ASFV). ASF has a short development of disease and a mortality rate close to 100%. Therefore, ASF is listed as a statutory reporting animal disease by the World Organization for Animal Health (Office international des epizooties, OIE), and it is also listed as the Class-I animal disease in China.

The development of recombinant strains of ASFV and related vaccines is one of the important means to deal with ASF.

Up to now, structural proteins and some non-structural proteins of many viruses cannot be directly knocked out by gene editing technology, making it impossible to clarify the role and the assembly mechanism of the viral protein during virus replication. A D1133L gene encoded by ASFV is a non-structural protein, which has a similar helicase motif to D6R of a vaccinia virus, belongs to the helicase, and is predicted to play a role in virus replication. The D1133L is a late-expressed gene.

An enzyme encoded in a Lac operon, under negative regulation of a lac repressor, Lactose operon repressor (LacI), can specifically bind to a lac operator gene(LacO) and further bind to a 21-bp sequence of the gene with a high affinity, repressing enzyme expression. The Lactose operon repressor (LacI) can also bind to allolactose or IPTG, thereby reducing the affinity of the repressor to the operon. In this way, IPTG can reduce inhibition of Lac operon transcription, thereby inducing expression of Lac operon. The system can well regulate the expression of transfected and integrated genes in mammalian cells, and is also used in the field of viruses. For example, the system has been used in the vaccinia virus (VACV) to study virus morphogenesis (MENG X, EMBRY A, ROSE L, et al. Vaccinia virus A6 is essential for virion membrane biogenesis and localization of virion membrane proteins to sites of virion assembly [J]. *J Virol*, 2012, 86(10): 5603-5613.), which becomes a powerful tool for transcriptional regulation of viral protein-host interactions.

SUMMARY

In the present disclosure, it is firstly found that the D1133L protein of ASFV can inhibit mRNA expression of IFN-β and downstream cytokines ISG-15 and ISG-56, with immunosuppressive effect. Secondly, in the present disclosure, a recombinant virus of ASFV knocking out a D1133L gene is constructed using an IPTG-induced expression system, to reduce the immunosuppressive activity of ASFV.

Specifically, the present disclosure provides use of the D1133L protein of ASFV in preparation of a drug for inhibiting expressions of IFN-β and downstream antiviral cytokines ISG15 and SG56.

The present disclosure further provides an attenuated strain of ASFV with IPTG-induced deletion of the D1133L gene, the attenuated strain of ASFV is obtained by cloning about 1.0 kb of a downstream sequence of the D1133L gene and about 1.0 kb of an upstream sequence of a D117L gene into pUC118 as the left homologous arm and the right homologous arm, respectively, and inserting a p72-eGFP-U104L-LacI-p72-LacO screening expression cassette between the left homologous arm and the right homologous arm to obtain a homologous recombinant transfer vector; and conducting homologous recombination on the homologous recombinant transfer vector with a wild ASFV. Such that the p72-eGFP-U104L-LacI-p72-LacO screening expression cassette is inserted into a position before the non-structural protein gene D1133L of the wild ASFV to obtain a recombinant virus ASFV vD1133Li; where the recombinant virus includes sequences of lad and lacO.

In the recombinant virus ASFV vD1133Li, LacI is a regulatory gene that can regulate the activity of the operator, and the regulatory gene can be transcribed into mRNA to synthesize a protein called repressor. In the absence of IPTG, the repressor can recognize and bind to the operator due to the conformation of the repressor. Therefore, the RNA polymerase cannot bind to a promoter gene, and a structural gene is also inhibited. As a result, the structural gene cannot be transcribed into mRNA to translate the D1133L protein. In the presence of IPTG, lactose metabolism produces allolactose that can bind to the repressor produced by the regulatory gene, such that the repressor changes its conformation and can no longer bind to the operator, thus the repressive effect is lost. As a result, the RNA polymerase binds to the promoter gene, activates the structural gene to be transcribed into mRNA, thereby translating the D1133L protein. lacO controls the rate of gene transcription and does not synthesize mRNA.

In the presence of IPTG, the obtained recombinant virus has similar characteristics to a wild-type virus; and in the absence of IPTG, the expression of the D1133L protein is inhibited.

The attenuated strain of ASFV with IPTG-induced deletion of a D1133L gene is a recombinant virus constructed using an ASFV CN/GS 2018 isolate strain.

A preparation method of the recombinant virus specifically includes the following steps: (1) Construction of an eGFP screening expression cassette: Amplifying an eGFP gene using a peGFP-N1 vector (the peGFP-N1 vector is purchased from Lanzhou Ruibolai Biotechnology Co., Ltd.) as a template for later use; amplifying a p72 promoter (a sequence from −196 nt to +17 nt upstream of a p72 gene) by PCR using an ASFV CN/GS 2018 as a template for later use; ligating the p72 promoter and the eGFP gene by fusion PCR. Synthesizing the LacI initiated by a U104L promoter and LacO initiated by the p72 promoter are synthesized; ligating the p72 promoter, the eGFP gene, U104L-LacI, and p72-LacO to obtain a screening expression cassette, named p'72-eGFP-U104L-LacI-p72-LacO.

(2) Construction of the homologous recombinant transfer vector: cloning about 1.0 kb of a downstream sequence of the D1133L gene and about 1.0 kb of an upstream sequence of a D117L gene a backbone vector pUC118 as the left homologous arm and the right homologous arm, respectively, and inserting a p72-eGFP-U104L-LacI-p72-LacO screening expression cassette between the left homologous arm and the right homologous arm, and after sequencing correctly to obtain a homologous recombinant transfer vector, named pUC-p72-eGFP-U104L-LacI-p72-LacO. Extracting the plasmid DNA with an endotoxin removal plasmid extraction kit, determining the concentration of the extracted plasmid DNA, and storing it at −20° C. for later use. A construction strategy is shown in FIG. 4.

The complete sequence of the complete D1133L gene is the nucleotide sequence of 139945th to 143346th of the genomic sequence of the ASFV CN/GS 2018 isolate strain, and the nucleotide sequence of 139945th to 143346th is shown in SEQ ID NO: 4.

(3) Cell transfection and recombinant virus screening: transfecting the homologous recombinant transfer vector pUC-p72-eGFP-U104L-LacI-p72-LacO into swine bone marrow-derived macrophages (BMDMs) ($10^6$ cells/well) with 4 μL of a JetPEI®-Macrophage DNA transfection reagent; after 6 h of transfection, infecting ASFV CN/GS 2018 directly without changing the medium; 48 h after infection, observing the number of fluorocytes with a fluorescence microscope; digesting the cells, picking all fluorocytes in each wells, carefully blowing them away in a new culture dish, and settling the fluorocytes for 1 h; picking all single fluorocytes, subjected to repeated freezing and thawing, and inoculating into pre-plated BMDM cells in a 96-well plate; observing every 12 h to find the cell wells with fluorescence, labeling the cell wells, and continuing to observe until 72 h. Sporadic green fluorescence can be seen under the fluorescence microscope, which is regarded as suspected recombinant virus-infected cells. Picking the fluorocytes carefully blowing them away in a new culture dish, settling the fluorocytes for 1 h; picking a single fluorocyte, subjected to repeated freezing and thawing 3 times after collection, and inoculating it into pre-plated PAM cells in a 96-well plate; observing every 12 h to find the cell wells with fluorescence, labelling the cell wells, and continuing to observe until 72 h. All-positive wells is wells with 100% of the fluorocytes, indicating that the recombinant virus construction is basically successful.

(4) Recombinant virus identification: in the presence of 1.5 μmol of IPTG, conducting 10 times of limited dilution expansion culture of the all-positive wells; picking and digesting the cell wells with 11th-generation recombinant virus into single cells, carefully aspirating 10 fluorocytes, inoculating them into the pre-plated PAM cells in a 96-well plate, and continuing to grow for 72 h. Picking the cells with more GFP fluorescence, extracting genomes from the wild ASFV and the gene-deleted ASFV using a virus genome extraction kit (purchased from TIANGEN Biotech (Beijing) Co., Ltd.), and conducting a PCR identification with primers for D1133L to identify whether the deletion is successful. By adding IPTG, expansion culture, purity test, and assay of a target gene by Western Blot (WB), it is determined that the expression of D1133L protein is inhibited in the purified ASFV vD1133Li in the absence of IPTG.

The primers for the D1133L gene include D1133L-F: 5'-C A T G C A C T T C G G T G A A A A A C T-3' (SEQ ID NO:8), and D1133L-R: 5'-GAGAATACATAAGGGTTTGCGT-3' (SEQ ID NO:9).

The present disclosure has the following beneficial effects:

In the present disclosure, it is firstly found that the D1133L protein of ASFV can inhibit IFN-β and downstream antiviral cytokines ISG15 and SG56, with an immunosuppressive effect.

The preparation method of the attenuated strain of ASFV with IPTG-induced deletion of a D1133L gene can conditionally control the expression of the D1133L gene in terms of time and quantity. The *Escherichia coli* lac operator-repressor system provides a powerful tool to study the role of ASFV genes in virus assembly, enabling molecular linkage to morphogenetic events. Likewise, conditional expression of viral genes can aid in understanding transcriptional regulatory mechanisms, as well as molecular interactions involved in virus-host relationships, such as viral infectivity or modulation of immune responses.

BRIEF DESCRIPTION OF THE DRAWINGS

FIG. 1A shows a detection result of ISG-56 mRNA; FIG. 1B shows a detection result of IFN-β mRNA; FIG. 1C shows a detection result of ISG-15 mRNA; Mock is non-transfected B-DNA, B-DNA is transfected B-DNA; and EV is non-transfected D1133L expression plasmid, and 130 is transfected D1133L expression plasmid.

FIG. 2 shows a schematic diagram of the construction strategy of a recombinant virus ASFVAD1133L with directly deleted D1133L gene of the ASFV.

FIG. 3 shows a passage survival state of the recombinant virus ASFVAD1133L with directly deleted D1133L gene of the ASFV; where TRANS refers to a bright field, eGFP refers to a green channel.

FIG. 4 shows a construction strategy of a genome of a recombinant virus ASFVvD1133Li.

FIG. 5 shows a situation of suspected recombinant virus infection of cells 6 h after transfection with a homologous recombinant transfer vector, inoculation with the AFSV CN/GS 2018 strain (MOI=0.1), and continuing to culture for 48 h, with a scale bar of 400 μM; where TRANS refers to a bright field, eGFP refers to a green channel.

FIG. 8A and FIG. 8B show a comparison of the mRNA level of D1133L in the cell line MA-104/D1133L and the control cell line pCDH-MA-104 when the multiplicity of infection (MOI) of an initial infection is 2 and the MOI is increased to 4, respectively; and MA-104 represents the cell line pCDH-MA-104.

INFORMATION OF BIOLOGICAL DEPOSIT

Figure 1A:
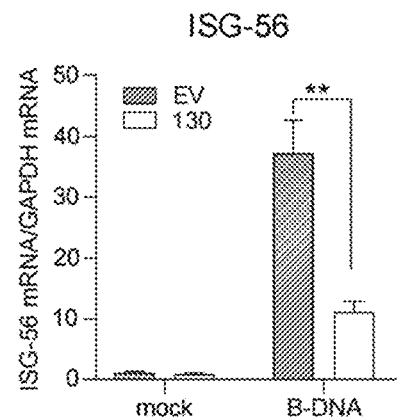
FIGS. 1A, 1B and 1C are detection results shows that ASFV D1133L protein inhibits mRNA expression of IFN-β and downstream cytokines; where

Type II African Swine Fever Virus Strain ASFV CN/GS 2018:
Date of deposit: Dec. 21, 2020;
Institution of deposit: China Center for Type Culture Collection (CCTCC);
Deposit number: CCTCC NO: V202096;
Address: Wuhan University, China;
Classification and Nomenclature: Type II African swine fever virus strain ASFV CN/GS 2018.
Vero Cells MA-104/D1133L:
Date of deposit: May 14, 2021;
Institution of deposit: China Center for Type Culture Collection (CCTCC);
Deposit number: CCTCC NO: C2021129;
Address: Wuhan University, China;
Classification and Nomenclature: Vero cells MA-104/D1133L.

DETAILED DESCRIPTION OF THE EMBODIMENTS

The present disclosure is further described by detail description of the specific embodiments, to facilitate understanding of the technich technical scheme of the present disclosure, but the claimed scope of the present disclosure is not limited thereto.

Biosafety permission and ASF laboratory activity permission: according to the relevant requirements of biosafety level 3 (BSL-3) laboratory and ASF-related biosafety, a premission of the Ministry of Agriculture to conduct research on highly-pathogenic ASFV pathogens and animals is obtained Lanzhou Veterinary Research Institute of the Chinese Academy of Agricultural Sciences, It is filed with the Ministry of Agriculture and Rural Affairs and is met the requirements of the national biosafety level, by submitting through Biosafety Committee of the Lanzhou Veterinary Research Institute, Laboratory Animal Ethics Committee, Biosafety Committee of the Chinese Academy of Agricultural Sciences, and the Laboratory Animal Ethics Committee of the Lanzhou Veterinary Research Institute.

Material Sources Used in the Examples:
Cells and Viruses:
Primary porcine alveolar macrophages (PAMs) and primary BMDMs are isolated from healthy swines aged 2 to 4 months (purchased from the Animal Center of the Lanzhou Veterinary Research Institute of the Chinese Academy of Agricultural Sciences); after aseptic collection of cells, red blood cells are removed with a red blood cell lysate (purchased from Biosharp), centrifuged at a low speed, and the supernatant is discarded; the cells are resuspended in an RPMI 1640 complete medium (purchased from Gibco) containing 10% FBS and cultured in a 37° C., 5% $CO_2$ incubator.

For cell culture of the BMDM, an additional 10 ng/mL final concentration of recombinant porcine GM-CSF (purchased from R&D Systems) is added to the RPMI 1640 complete medium, placed in a 37° C., 5% $CO_2$ incubator for induction, and washed once every 2 d to 3 d; the non-adherent cells are centrifuged and added to a new cell flask, the medium is changed to continue the induction, followed by cryopreservation or use after 3 d to 7 d. ASFV is amplified by PAMs and a virus titer is determined. BMDMs are used for plasmid transfection and virus recombination experiments.

An ASFV strain CN/GS 2018 is isolated in a P3 laboratory of the Lanzhou Veterinary Research Institute of the Chinese Academy of Agricultural Sciences, and deposited in the CCTCC, with a deposit number of CCTCC NO: V202096; the ASFV strain belongs to genotype II, with a virus titer of $10^6 HAD_{50}/100$ μL, and is stored in aliquots at $-80°$ C. for later use. A peGFP-N1 vector and a pUC57 vector each are purchased from Lanzhou Ruibolai Biotechnology Co., Ltd.; an endotoxin-free plasmid extraction kit is purchased from OMEGA. HEK-293T cells are preserved by the laboratory; and B-DNA is purchased from Lanzhou Ruibolai Biotechnology Co., Ltd.

The experimental methods in the following examples, unless otherwise specified, are operating methods known in the art; the test materials used in the following examples, unless otherwise specified, are purchased from conventional biochemical reagent companies.

Example 1 Immunosuppressive Effect of ASFV D1133L Protein

HEK-293T cells were plated into individual wells of a 24-well plate. When the cells grew to 70% to 80% of fusion, a D1133L expression plasmid was transfected using a liposome reagent (200 ng/well). Construction of the D1133L expression plasmid: 5'(NotI), 5'UTR ([g], 3'(SalI) were added to a D1133L gene, and the gene was cloned into a vector p3×FLAG-CMV-7.1 (Amp+) via 5' NotI and 3' SalI.

After 24 h of transfection, B-DNA (1000 ng/well) was transfected again with liposome, and the supernatant was collected after 12 h of transfection, and the total cell RNA was extracted; after reverse transcription, RT-qPCR was conducted to detect the expression levels of IFN-β and downstream antiviral cytokines ISG-15 and ISG-56.

Figure 1B:
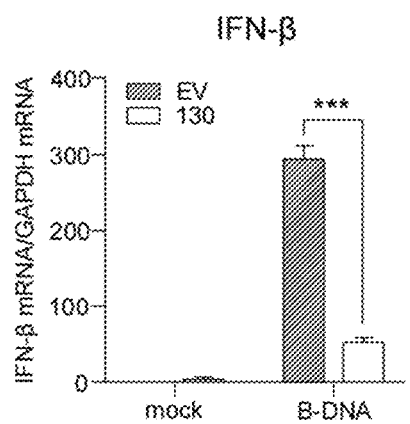
Figure 1C:
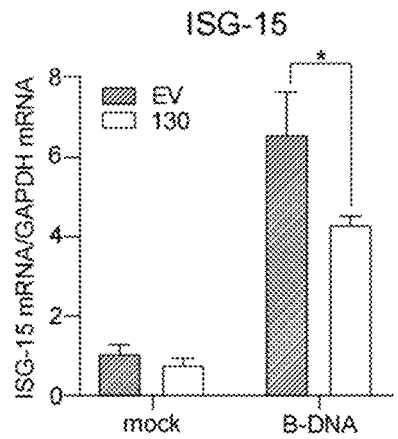

The detection results were shown in FIGS. 1A, 1B and 1C. The results showed that compared with the samples without B-DNA transfection, the mRNA expressions of IFN-β and downstream cytokines ISG-15 and ISG-56 in cells were significantly increased after B-DNA transfection; while compared with the untransfected D1133L expression plasmid group, after co-transfection of B-DNA and D1133L expression plasmid (200 ng/well), the mRNA expressions of IFN-β and downstream cytokines ISG-15 and ISG-56 in the cells were significantly reduced. This showed that D1133L could inhibit the mRNA expressions of B-DNA-induced IFN-β and downstream cytokines ISG-15 and ISG-56, and indicating that D1133L may have an immunosuppressive effect.

In conclusion, the ASFV D1133L protein could inhibit the expressions of IFN-β and downstream antiviral cytokines ISG-15 and ISG-56, with an immunosuppressive effect.

An RT-qPCR reaction system (10 μL) included: 5 μL of a SYBR Permix Ex Taq II, 0.5 μL of an upstream primer, 0.5

μL of a downstream primer, 3 μL of DEPC water, and 1 μL of a cDNA. A reaction program included: initial denaturation at 95° C. for 3 min; 40 cycles of denaturation at 95° C. for 10 sec, annealing and extension at 60° C. for 34 sec. The relative mRNA levels of these genes were normalized to porcine GAPDH mRNA levels, and primer sequences were shown in Table 1.

TABLE 1

Primer sequence listing

| Primer name | Base sequence (5'-3') |
|---|---|
| hISG56-F | CTTGAGCATCCTCGGGTTCATC (SEQ ID NO: 10) |
| hISG56-R | AAGTCAGCAGCCAGGTTTAGGG (SEQ ID NO: 11) |
| hISG15-F | TGGACAAATGCGACGAACC (SEQ ID NO: 12) |
| hISG15-R | CCCGCTCACTTGCTGCTT (SEQ ID NO: 13) |
| hIFN-β-F | GACATCCCTGAGGAGATTAAG (SEQ ID NO: 14) |
| hIFN-β-R | ATGTTCTGGAGCATCTCATAG (SEQ ID NO: 15) |
| hGAPDH-F | CGGGAAGCTTGTGATCAATGG (SEQ ID NO: 16) |
| hGAPDH-R | GGCAGTGATGGCATGGACTG (SEQ ID NO: 17) |

Example 2 ASFV Cannot Survive and Passage after Direct Deletion of D1133L Gene of ASFV To facilitate screening, a set of expression cassettes were constructed for screening marker genes: a p72 promoter (a sequence from −196 nt to +17 nt upstream of a p72 gene) was amplified by PCR for later use; an eGFP gene was amplified using a peGFP-N1 vector as a template for later use; the obtained amplified p72 promoter and eGFP were ligated with SV40polyA to obtain p'72-eGFP-SV40polyA (set forth in SEQ ID NO: 1); the expression cassette sequence included an SV40polyA termination sequence. A homologous recombinant transfer vector was constructed for D1133L gene knockout using a pUC57 vector as the backbone vector. The specific steps were: about 1 kb of upstream and downstream sequences of the D1133L gene were designed as homologous arms of recombination; a left homologous arm (Left arm, set forth in SEQ ID NO: 2) and a right homologous arm (Right arm, set forth in SEQ ID NO: 3) were cloned into the backbone vector pUC57 separately; a gene fragment of the p72-eGFP-SV40polyA screening expression cassette was inserted between gene sequences of the Left and Right arm of the D1133L recombinant transfer vector. After sequencing correctly, the homologous recombinant transfer vector was named pUC-LRAD1133L-eGFP; a plasmid DNA was extracted with an endotoxin-removed plasmid extraction kit, subjected to concentration determination, and was stored at −20° C. for later use. The complete D1133L gene had a nucleotide sequence set forth in SEQ ID NO: 4. A sequence of D1133L gene was a nucleotide sequence of 139945th to 143346th of a genomic sequence of the ASFV CN/GS 2018 isolate strain.

The homologous recombinant transfer vector pUC-LRAD1133L-eGFP (2 μg) was transfected into swine BMDMs with a JetPEI®-Macrophage DNA transfection reagent ($10^6$ cells/well); after 6 h of transfection, ASFV CN/GS 2018 was infected directly, without changing the medium; until 48 h after infection, the number of fluorocytes were observed under a fluorescence microscope; the cells were digested, all fluorocytes in each wells were picked, carefully blown away in a new culture dish, and settled for 1 h; all single fluorocytes were picked, subjected to repeated freezing and thawing, and inoculated into pre-plated BMDM cells in a 96-well plate; the cells were observed every 12 h to find cell wells with fluorescence, the cell wells were labeled, and the observation was continued until 72 h; sporadic green fluorescence could be seen under the fluorescence microscope, which was regarded as suspected recombinant virus-infected cells. The fluorocytes were picked, carefully blown away in a new culture dish, and settled for 1 h; the single fluorocyte was picked, subjected to repeated freezing and thawing 3 times after collection, and inoculated into pre-plated PAM cells in a 96-well plate; the cells were observe every 12 h to find cell wells with fluorescence, the cell wells were labeled, and the observation was continued until 72 h. All-positive wells were wells with 100% of the fluorocytes, indicating that a construction of recombinant virus was basically successful. The construction strategy was shown in FIG. 2.

Figures 2, 3:
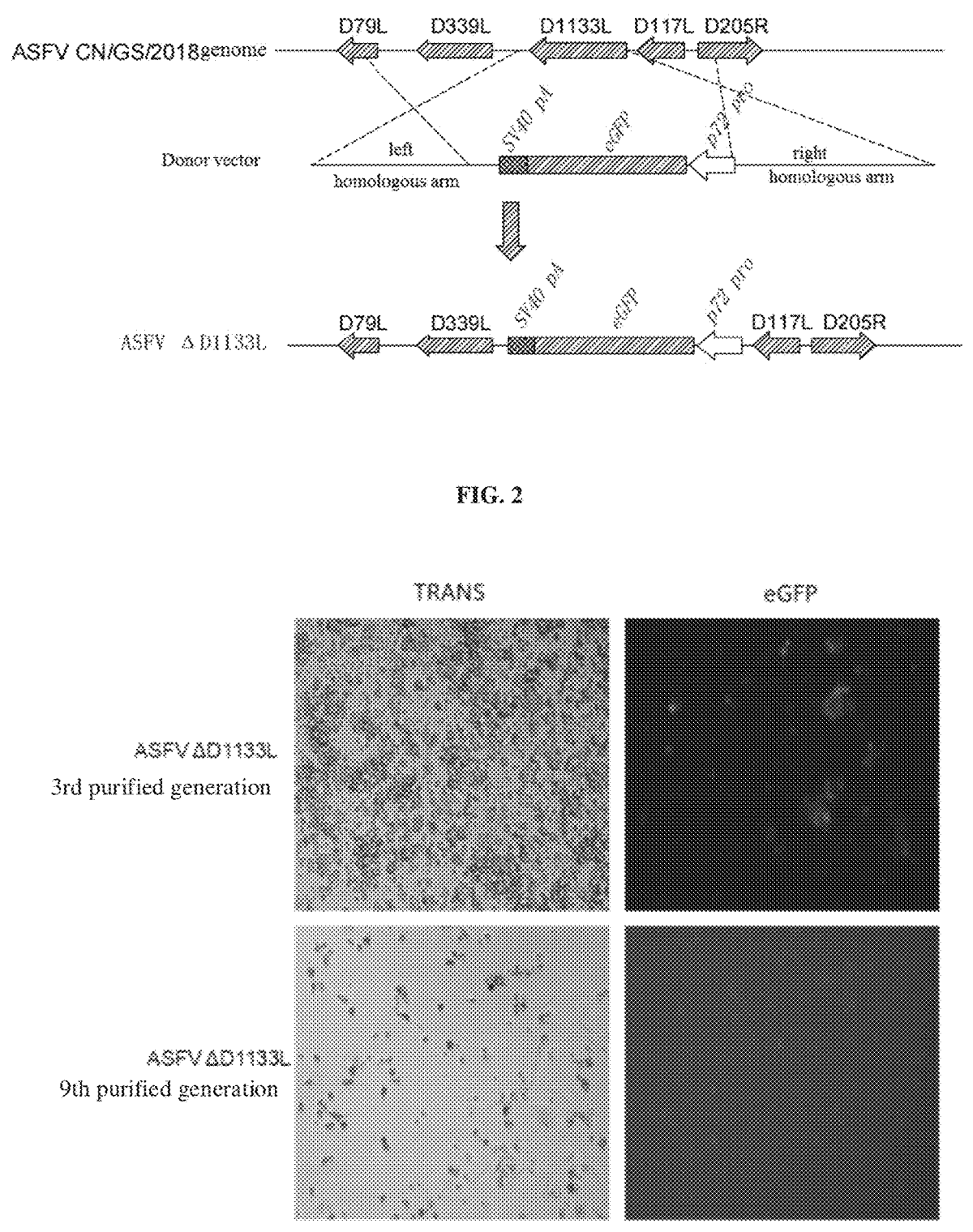

The passage survival state of the recombinant virus ASFVAD1133L was shown in FIG. 3. The results showed that ASFV cannot survive and passage after direct deletion of the D1133L gene of ASFV.

Figures 4, 5:
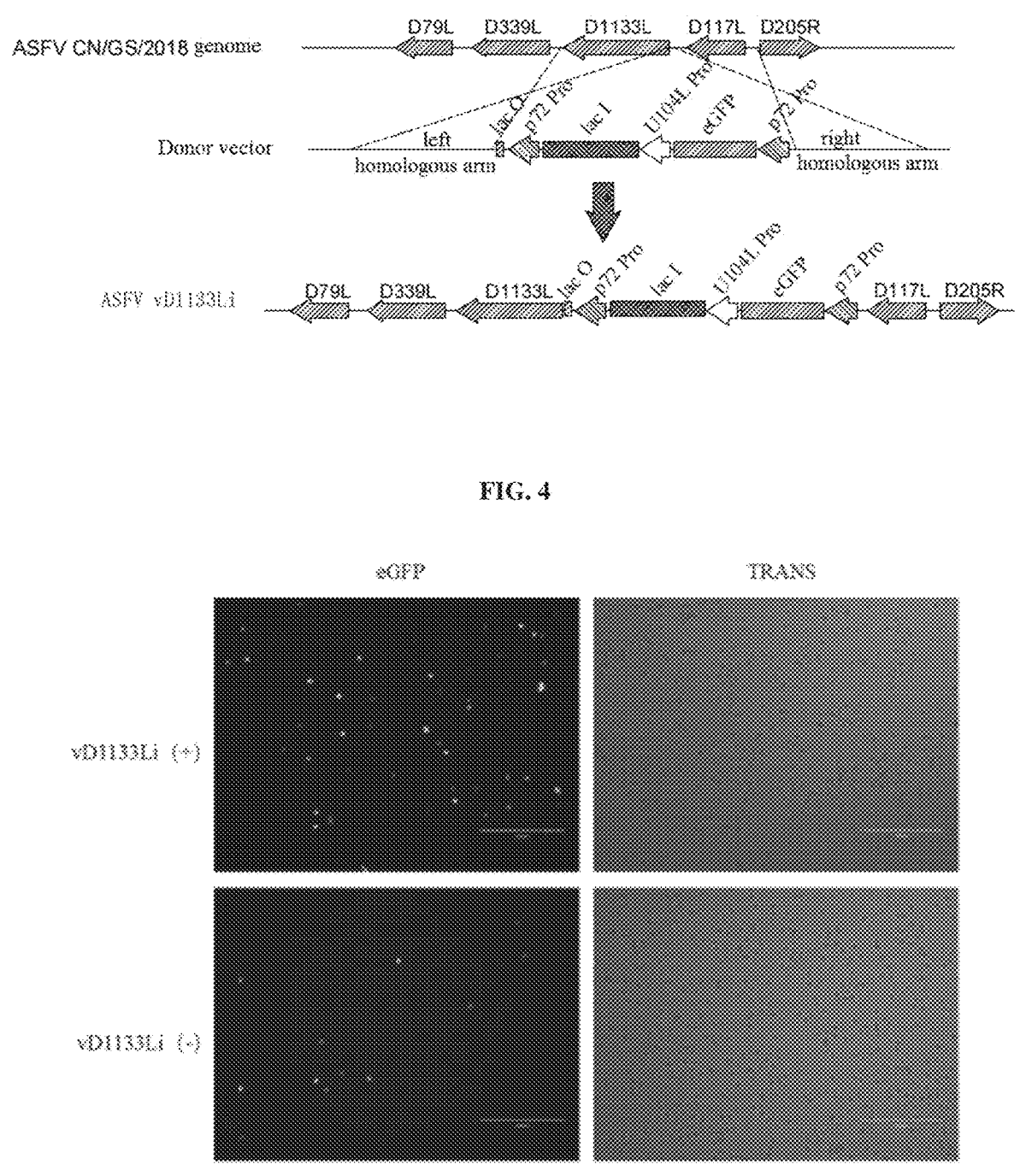

Example 3 Construction, Purification and Identification of Attenuated Strain of ASFV with Inducible Deletion of D1133L Gene FIG. 4 showed a construction strategy of the recombinant virus.

1.1. Construction of eGFP Screening Expression Cassette

The screening cassette included three parts. The first part, ASFV CN/GS 2018 was used as a template to amplify the p72 promoter sequence by PCR (reference (O'Donnell V, Holinka L G, Krug P W, Gladue D P, Carlson J, Sanford B, Alfano M, Kramer E, Lu Z, Arzt J, Reese B, Carrillo C, Risatti G R, Borca M V. African Swine Fever Virus Georgia 2007 with a Deletion of Virulence-Associated Gene9GL (B119L), when Administered at Low Doses, Leads to Virus Attenuation in Swine and Induces an Effective Protection against Homologous Challenge. *J Virol.* 2015; 89(16): 8556-66)). The p72 promoter was amplified by PCR (a sequence from −196 nt to +17 nt upstream of a p72 gene) for later use; meanwhile, an enhanced green fluorescent protein (eGFP) gene was amplified by the peGFP-N1 vector as a template. The second part, synthesis of LacI initiated by U104L promoter. The third part, synthesis a LacO system initiated by p72 promoter. The three parts were ligated to obtain a gene fragment of the eGFP screening expression cassette, named p72-eGFP-U104L-LacI-p72-LacO (shown in SEQ ID NO: 5).

1.2. Construction of Homologous Recombinant Transfer Vector

A homologous recombinant transfer vector was constructed for conditional gene knockout of D1133L using a pUC118 vector as a backbone vector.

The specific steps were: about 1.0 kb of a downstream sequence of D1133L gene and about 1.0 kb of an upstream sequence of D117L gene were designed as the left recombinant homologous arm (shown in SEQ ID NO: 6) and the right recombinant homologous arm (shown in SEQ ID NO: 7), respectively; the left and right recombinant homologous arms were cloned into the backbone vector pUC118 (inserted into XmaJI and HindIII restriction sites, respectively); and a p72-eGFP-U104L-LacI-p72-LacO screening expression cassette fragment was inserted between the two homologous arms. After sequencing correctly, the homologous recombinant transfer vector was named pUC-p72-eGFP-U104L-LacI-p72-LacO; a plasmid DNA was extracted with an endotoxin-removed plasmid extraction kit, subjected to concentration determination, and stored at −20° C. for later use.

1.3. Cell Transfection and Recombinant Virus Screening

The homologous recombinant transfer vector pUC-p72-eGFP-U104L-LacI-p72-LacO (4 μg) was transfected into swine BMDMs ($10^6$ cells/well) with 6 μL of a JetPEI®-Macrophage DNA transfection reagent. After 6 h of transfection, the complete medium was discarded; BMDMs were directly infected with an purified virus strain of ASFV CN/GS 2018 (MOI=1), 1.25 mM IPTG was added, and the medium was not changed after infection; after 48 h, the number of fluorocytes was observed with a fluorescence microscope and the fluorocytes were photographed. A large amount of fluorescent expression could be observed under the microscope, indicating that the suspected recombinant virus infected cells successfully (FIG. 5).

After cell digestion, all fluorocytes were picked in each well, carefully blown away in a new culture dish, and settled for 1 h; a single fluorocyte was picked in each infection well, subjected to repeated freezing and thawing, and inoculated into pre-plated BMDM cells in a 96-well plate; the cells were observe every 12 h to find cell wells with fluorescence, the cell wells were labeled, and continued to be observed until 72 h. The results showed that the proportion of fluorocytes in some wells could reach 100%, indicating that the recombinant virus was successfully constructed, named ASFVvD1133Li.

1.4. Purification and Identification of Recombinant Virus

Figure 6:
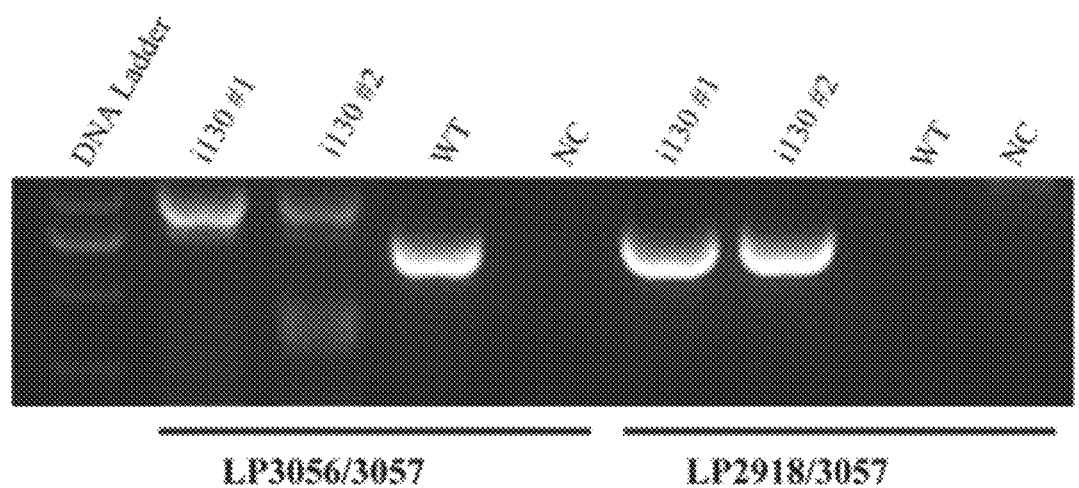
FIG. 6 shows PCR identification results after purification of the recombinant virus, where i130#1 and i130#2 are two recombinant viruses, WT is an ASFV CN/GS2018 wild strain, and NC is a negative control with water as a template.

IPTG was added to purify the positive wells; 100% positive wells were subjected to 10 times of limited dilution expansion culture to obtain the recombinant virus, during which genomic DNAs of the wild ASFV and recombinant ASFV were extracted with a viral genome extraction kit (purchased from TIANGEN Biotech (Beijing) Co., Ltd.); the recombinant virus was identified by PCR using endogenous detection primers for D1133L gene (the endogenous detection primers were LP3056/LP3057, with an amplification length of 629 bp (LP3056-130endoSur-F: 5'-gtgattgcctgctgtttagtctt-3' (SEQ ID NO:18); LP3057-130endoSur-R: 5'-caggacgtcttagcatttctgtt-3'(SEQ ID NO:19)), and exogenous detection primers for the homologous arms (the exogenous detection primer was LP2918/LP3057, with an amplification length of 723 bp (LP2918/LP3057, 5'-gacctgcaggcatgccgtac-3' (SEQ ID NO:20))). The results showed that under the induction of IPTG, the D1133L gene had been detected in the genome of the recombinant virus, as shown in FIG. 6.

1.5. Recombinant Virus Infection of Cells

PAM cells were plated on a 6-well plate and cultured for 12 h; after being adhered to 80%, the cells were infected with ASFVvD1133Li; after 2 h, the medium was replaced with a new one containing IPTG (1.25 mM), and a medium without IPTG was used as control; after 48 h of infection, fluorescence was observed by a fluorescence microscope.

The results were shown in FIG. 5. It could be seen from the fluorescence microscope that after PAM cells were infected by ASFVvD1133Li for 48 h, in the presence of IPTG, the number of virus fluorescence was significantly higher than that in the absence of IPTG. This indicated that in the absence of D1133L, viral replication was significantly reduced.

1.6. One-Step Growth Curve Experiment

PAM cells ($1 \times 10^6$) were plated in a 12-well plate and cultured with a 10% RMPI1640 medium for 12 h; after being adhered to 80%, the cells were infected with ASFV CN/GS 2018 strain (WT) and the recombinant strain ASFVvD1133Li; after 2 h, the medium was discarded and a new medium was replaced; the recombinant strain ASFV vD1133Li group was further divided into a group with IPTG (1.25 mM) (vD1133Li(+)) and a group without IPTG (vD1133Li(−)); samples were collected at different time points of 6 h, 12 h, 24 h, 48 h, 64 h and 72 h. The samples were placed at −80° C. and room temperature for freezing and thawing 3 times, and inactivated in a metal bath at 100° C. for 10 min; a viral DNA was extracted with a DNA extraction kit, and a viral copy number was detected by probe-based RT-PCR.

Figure 7:
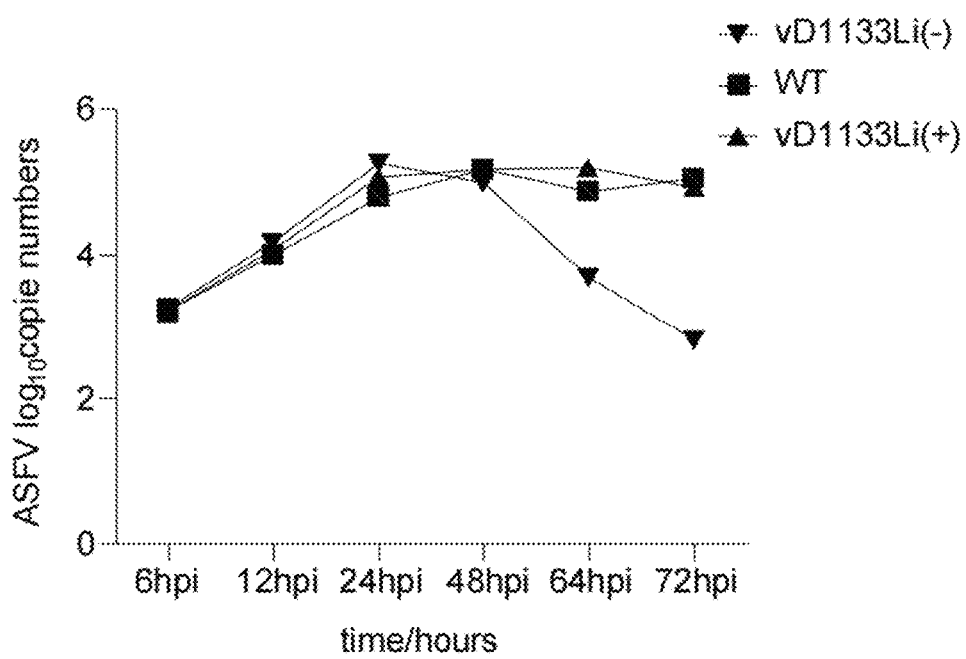
FIG. 7 shows a comparison result of replication of the recombinant virus ASFV vD1133Li and a parental strain in PAM cells (one-step growth curve); where vD1133Li(−) means in the absence of IPTG, vD1133Li(+) means in the presence of IPTG, and WT is an ASFV CN/GS2018 strain.

The results were shown in FIG. 7: a growth curve of the recombinant strain ASFV vD1133Li group after adding IPTG (1.25 mM) was similar to that of the ASFV CN/GS 2018 strain (WT) group.

Example 4 Recovery of Replication Ability of Recombinant Virus ASFV vD1133Li without IPTG Induction MA-104 cells were preserved by a foot-and-mouth disease epidemiology team of the Lanzhou Veterinary Research Institute of the Chinese Academy of Agricultural Sciences. JetPEI®-Macrophage was purchased from Beijing Dakewe Biotechnology Co., Ltd.; DMEM, 0.25% EDTA trypsin and FBS each was purchased from ThermoScientific; PBS was purchased from Hyclone; an ECL chromogenic kit and mouse anti-β-actin monoclonal antibody each was purchased from ThermoScientific; an NP-40 lysate and PMSF each was purchased from Beyotime; and a reverse transcription kit was produced by Novozymes. The ASFV D1133L monoclonal antibody was prepared by the foot-and-mouth disease epidemiology team of Lanzhou Veterinary Research Institute. A preparation method was detailed in patent with publish number of CN112481220A. Immunofluorescence rabbit secondary antibody was purchased from CST, rabbit secondary antibody was purchased from Proteintech Group.

1. Construction of MA-104/D1133L Cell Line Stably Expressing D1133L 1.1. Construction of Lentiviral Vector and Viral Packaging Specifically, the method included the following steps:

Step 1, construction of recombinant lentiviral vectors Lv-D1133L and Lv-pCDH: the D1133L gene was synthesized by chemical synthesis, where a gene sequence was set forth in NC 044959.2 on NCBI; EcoRI and NotI restriction sites were introduced into a 5'-end and a 3'-end of the D1133L gene, and the synthesized D1133L gene was religated with the lentiviral vector Lv-pCDH vector to obtain a recombinant lentiviral vector Lv-D1133L. The recombinant plasmid was identified by double enzyme digestion with EcoRI and NotI.

Step 2, Lentivirus Packaging:

(1) 293T Cells were Used to Package Viral Solutions of the Lentivirus Lv-pCDH and Lv-D1133L;

1) Digestion and Inoculation of 293T Cells:

The well-grown 293T cells were digested with 0.25% trypsin to prepare a single cell suspension and adjusted to a concentration of $4 \times 10^5$ cells/mL, and 10 mL of the single cell suspension was inoculated into a 10 cm culture dish. Incubation was conducted overnight in a 37° C., 5% $CO_2$ incubator, and the cell was prepared for later use until next day the cell confluency reached 80%.

2) Virus Package:

3 µg of a packaging plasmid pMD2G, 6 µg of psPAX and 7.5 µg of lentiviral vector plasmid Lv-D1133L or Lv-pCDH were added to 150 µL of OPTI-MEM and mixed to obtain a lentiviral vector mixture; 25 µL of Lipo 2000 was added to 500 µL of the OPTI-MEM, mixed well, and allowed to stand at room temperature for 5 min to obtain a Lipo 2000 mixture; the lentiviral vector mixture was slowly added to the Lipo 2000 mixture, mixed well, and allowed to stand at room temperature for 15 min. A resulting product was added dropwise to the 293T cells with 80% confluency obtained in 1), and mixed well. After 6 h, the medium was replaced with fresh DMEM containing 10% FBS.

Requirements of the Lentiviral Vectors: A Concentration of 1 µg/µL and a Purity: $OD_{260}/OD_{280}$ Value of 1.8 to 2.0.

(2) After culturing for 48 h, a culture solution was collected (containing lentivirus), centrifuged at 1,500 g at 4° C. for 10 min to remove cell debris, a virus supernatant was filtered with a 0.45 µm filter membrane, and then with a 0.45 µm filter, and stored for later use.

Figure 8A:
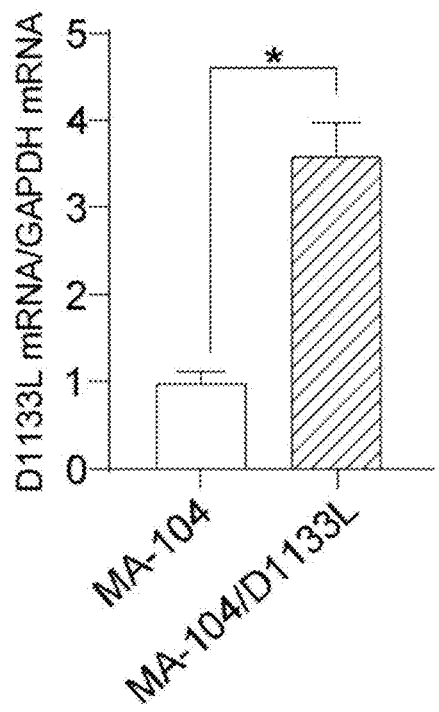
FIGS. 8A and 8B show a comparison of expression levels of D1133L in cell lines pCDH-MA-104 and MA-104/D1133L; where
Figure 8B:
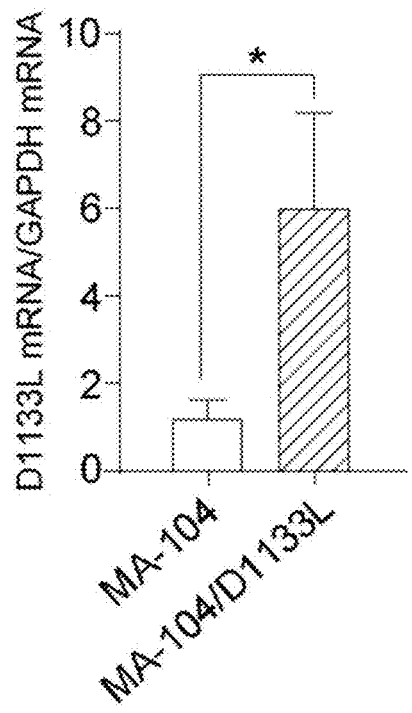

The lentivirus could be inserted into the cell genome, with stable expression, long duration, short packaging cycle, and an infection efficiency much lower than that of adenovirus. The lentivirus could not be amplified, and the virus needed to be repackaged if necessary after the one-time packaged virus was used up. When the lentivirus Lv-D1133L infected the target cells (MA104), after the first infection (MOI of 2), it was found that the expression level of D1133L was only three times more than that of empty cells (FIG. 8A), which was much lower than expected, indicating that the virus titer was low after infection with this method. Then the MOI was adjusted to 4 times of the initial MOI, and the amount of virus was increased to infect the target cells; meanwhile, the infection was conducted by polybrene as an auxiliary infection reagent at a final concentration of 2 µg/mL to 5 µg/mL, and a final expression level of D1133L was increased to 7.5 times that of the empty (FIG. 8B).

1.2. Screening and Identification of MA-104 Cell Line MA-104/D1133L Stably Expressing D1133L 1.2.1. Lentivirus Infection of MA-104 Cells The virus filtrate of Lv-pCDH and Lv-D1133L obtained in step 1.1 were added to a 5×pEGit virus Precipitation (BioVisionCatalog #K904-50/200) at a ratio of 4:1 separately. After allowing to stand at 4° C. overnight, centrifugation was conducted at 3,200 g for 20 min at 4° C. A supernatant was discarded, a virus pellet was resuspended in DMEM containing 5% FBS, aliquoted at 200 µL/tube, and stored at −80° C.

The MA-104 cells (10 cm petri dish) were infected with the lentivirus Lv-pCDH and Lv-D1133L, with a virus volume of 200 µL and a number of virus at about $2×10^7$, supplemented to 2 mL with a complete medium, and 2 µL of a transfection enhancer polybrene was added in a final concentration of 2 µg/mL to 5 µg/mL, MA-104 cells were infected (MOI=4), and the infection was terminated after 8 h. Two groups of cells were denoted as pCDH-MA-104 and MA-104/D1133L, respectively.

1.2.2. Screening of pCDH-MA-104 and MA-104/D1133L Cell Lines

After 48 h of infection, puromycin was added for drug screening; after screening for 48 h to 72 h, the medium was replaced and cells were passaged, and the culture was maintained to obtain positive cell lines pCDH-MA-104 and MA-104/D1133L. The positive cell line MA-104/D1133L obtained by screening was the MA-104 cell line stably expressing D1133L protein.

1.2.3. RT-qPCR Detection of D1133L Expression Level (1) RT-qPCR primers were designed for D1133L, and primer sequences were shown in Table 2.

TABLE 2

Primer sequence listing

| Primer name | Base sequence (5'-3') |
| --- | --- |
| D1133L-F | CTTCTGGAAAACGGGGTACA (SEQ ID NO: 21) |
| D1133L-R | CAAGATAAGAACCCCCGACA (SEQ ID NO: 22) |
| β-actin-human-F | AGAGCTACGAGCTGCCTGAC (SEQ ID NO: 23) |
| β-actin-human-R | AGCACTGTGTTGGCGTACAG (SEQ ID NO: 24) |
| GAPDH-F (M) | CATGTTCCAGTATGACTCCACT (SEQ ID NO: 25) |
| GAPDH-R (M) | GTAGACTCCACGACATACTCAG (SEQ ID NO: 26) |
| p30-F | CTCCGATGAGGGCTCTTGCT (SEQ ID NO: 27) |
| p30-R | AGACGGAATCCTCAGCATCTTC (SEQ ID NO: 28) |
| p72-F | TGCGATGATGATTACCTT (SEQ ID NO: 29) |
| p72-R | ATTCTCTTGCTCTGGATAC (SEQ ID NO: 30) |

(2) Trizol was used to extract RNA from positive pCDH-MA-104 and MA-104/D1133L cell lines, and the concentration of RNA was determined.

(3) The reverse transcription was conducted according to a standard of reverse transcription on 500 ng of RNA into cDNA in 10 µL system; RT-qPCR detection was conducted using a successfully reverse-transcribed cDNA as a template and the primers synthesized in step (1) as amplification primers. A reaction system included: 10 µL, of an AceQ® qPCRSYBR® Green Master Mix, 7.2 µL, of DEPC water, 0.4 µL, of a Primer 1 (10 µM), 0.4 µL, of a Primer 2 (10 µM), and 2 µL of the template cDNA. An amplification program included: 95° C. for 5 min; 40 cycles of 95° C. for 10 sec and 60° C. for 30 sec; 95° C. for 15 sec, 60° C. for 60 sec, and 95° C. for 15 sec. RT-qPCR results were shown in FIG. 8B. The results showed that the expression level of D1133L at the mRNA level in MA-104/D1133L cell line was about 7.5 times higher than that of the control cell line pCDH-MA-104.

Figure 9:
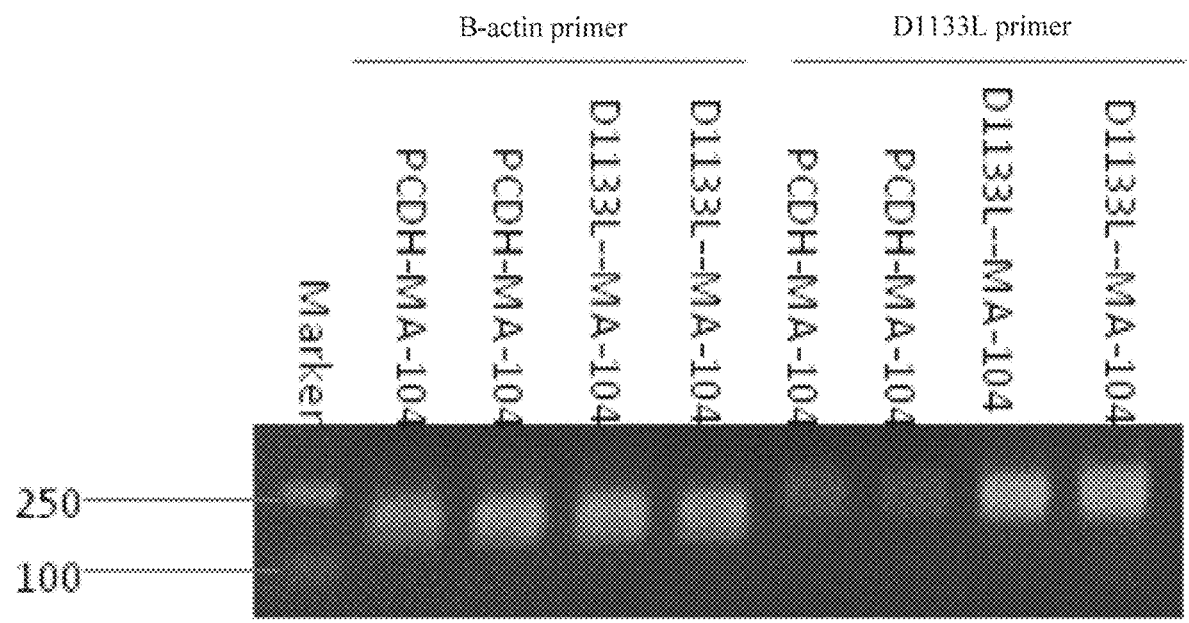
FIG. 9 shows electrophoresis detection images of qRT-PCR products of D1133L and β-actin of the cell lines pCDH-MA-104 and MA-104/D1133L; where D1133L-MA-104 represents the cell line MA-104/D1133L.

(4) After the RT-qPCR, products of RT-qPCR were detected by nucleic acid electrophoresis. The results were shown in FIG. 9: for the D1133L gene, the bands of the qRT-PCR amplification products of the MA-104/D1133L cell line were significantly different from those of the pCDH-MA-104 cell line; for the β-actin gene, the bands of the qRT-PCR amplification products of the two cell lines were basically the same. The qRT-PCR primer sequences of β-actin gene were shown in Table 2.

RT-qPCR detection and electrophoresis results showed that the cell line MA-104/D1133L stably expressing D1133L was screened; and D1133L could be efficiently and stably expressed in the cell line. The MA-104/D1133L was deposited in CCTCC, with a deposit number of CCTCC NO: C2021129.

2. Viral Gene Expression of MA-104 Cells Infected with ASFV vD1133Li Under IPTG Induction MA-104 cells were plated in a 12-well plate; when a cell density reached 70% to 80%, the cells were infected with ASFV CN/GS 2018 strain (WT) and recombinant strain ASFVvD1133Li separately, and a blank control mock was set up; the cells were cultured in serum-free DMEM for 2 h, the medium was discarded and replaced with DMEM with 2% FBS. The recombinant strain ASFVvD1133Li was divided into adding IPTG (1.25 mM) (vD1133Li(+)) and without adding IPTG (vD1133Li(-)); samples were collected after 36 h, and expression levels of ASFVD1133L, p30 and p72 were detected by Western blot assay.

Figure 10:
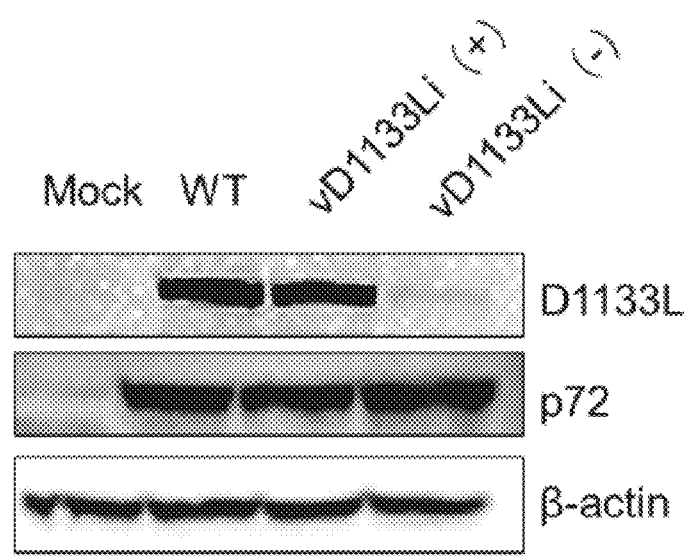
FIG. 10 shows gene expression of recombinant virus ASFV vD1133Li-infected MA-104.

The results were shown in FIG. 10: p30, p72 and D1133L expresses normally in the ASFV vD1133Li in the presence of IPTG; in the absence of IPTG, the D1133L was not expressed, while the p30 and p72 were expressed, with expression levels lower than those in the presence of IPTG.

3. Differences Between Recombinant Virus ASFV vD1133Li in MA-104/D1133L and MA-104 Cells MA-104/D1133L and MA-104 cells were inoculated in a 12-well plate at $1\times10^5$ cells/well, and infected with ASFV vD1133Li (MOI=1.5); after 36 h, a cell lysate was collected, washed with PBS, and 100 μl of a 1× loading protein loading buffer was added to lyse the cells, and 20 μl of a protein loading was collected for SDS-PAGE; after electrophoresis, the protein was transferred to NC membrane with 100 V constant pressure for 1.5 h, and a 5% nonfat milk powder prepared with TB ST was used for blocking at room temperature for 2.5 h; antibody dilutions were serially diluted as follows: primary antibody D1133L monoclonal antibody (1:1000), β-actin (1:5000), p30 (1:1000) and p72 (1:1000), and incubated overnight at 4° C.; 1×TBST prepared HRP-conjugated Affinipure Goat Anti-Rabbit IgG (H+L), Goat Anti-Mouse (1:10000) was incubated at room temperature for 2 h; and a resulted product was analyzed by fully-automated chemiluminescence imaging using a Western Bright ECL chemiluminescence substrate.

Figure 11A:
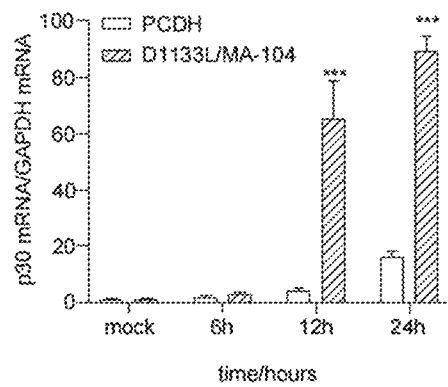
FIGS. 11A, 11B and 11C show a comparison of replication of the recombinant virus ASFV vD1133Li in MA-104/D1133L cell line and wild-type MA-104 cell line; where PCDH represents wild-type MA-104 cells, and D1133L/MA-104 represents MA-104/D1133L cells.
Figure 11B:
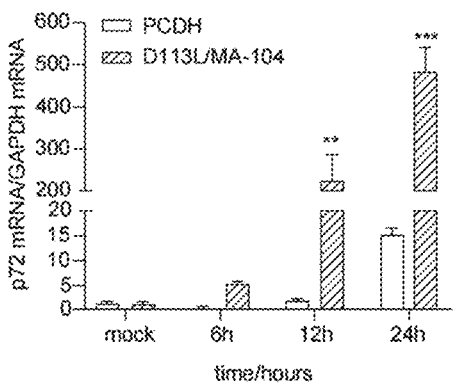
Figure 11C:
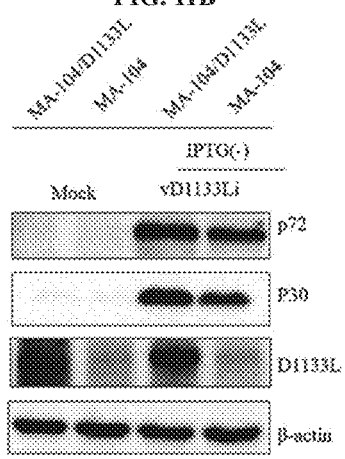

The results were shown in FIG. 11. In the absence of IPTG, ASFV vD1133Li could infect D1133L-overexpressing MA-104/D1133L cells and wild-type MA-104 cells, and the protein expressions of p30 and p72 are detected by western blot. The results showed that the protein expression levels of p30 and p72 in MA-104/D1133L cells were significantly higher than those in MA-104.

The above-mentioned examples are only preferred examples of the present disclosure, and do not limit the implementation scope of the present disclosure. Therefore, all equivalent changes or modifications made according to the structure, features and principles described within the scope of the present disclosure shall be included in the claimed scope of the present disclosure.

What is claimed is:

1. An attenuated strain of ASFV with IPTG-induced deletion of a D1133L gene, wherein the attenuated strain of ASFV is obtained by IPTG-induced deletion of the D1133L gene of an ASFV using an *Escherichia coli* lac operator-repressor system; and in the absence of the IPTG, an expression of a D1133L protein of the attenuated strain of ASFV is inhibited;

wherein the *Escherichia coli* lac operator-repressor system comprises a vector containing SEQ ID NO: 6, SEQ ID NO: 7 and SEQ ID NO: 5;

wherein the SEQ ID NO: 5 is inserted between SEQ ID NO: 6 and SEQ ID NO: 7.

2. The attenuated strain of ASFV with IPTG-induced deletion of a D1133L gene according to claim 1, wherein the ASFV is ASFV CN/GS 2018; and the D1133L gene has the nucleotide sequence set forth in SEQ ID NO: 4.

3. A method for preparing the attenuated strain of ASFV with IPTG-induced deletion of a D1133L gene according to claim 1, comprising the following steps: cloning a downstream sequence of the D1133L gene and an upstream sequence of a D117L gene into pUC118 as a left homologous arm and a right homologous arm, respectively, and inserting a p72-eGFP-U104L-LacI-p72-LacO screening expression cassette between the left homologous arm and the right homologous arm to obtain a homologous recombinant transfer vector; and conducting homologous recombination on the homologous recombinant transfer vector with a wild ASFV, obtaining a recombinant virus ASFV vD1133Li by inserting the p72-eGFP-U104L-LacI-p72-LacO screening expression cassette into a position before the D1133L gene of the wild ASFV.

4. The method according to claim 3, wherein the ASFV is ASFV CN/GS 2018.

5. The method according to claim 3, specifically comprising the following steps:
   (1) construction of an eGFP screening expression cassette by amplifying an eGFP gene and a p72 promoter; synthesizing LacI initiated by a U104L promoter and LacO initiated by the p72 promoter; ligating the p72 promoter, the eGFP gene, U104L-LacI, and p72-LacO to obtain a screening expression cassette, p72-eGFP-U104L-LacI-p72-LacO;
   (2) construction of a homologous recombinant transfer vector by designing the downstream sequence of the D1133L gene and the upstream sequence of the D117L gene as the left homologous arm and the right homologous arm, respectively, and cloning into a backbone vector pUC118; inserting the p72-eGFP-U104L-LacI-p72-LacO screening expression cassette between the left homologous arm and the right homologous arm to obtain the homologous recombinant transfer vector, pUC-p72-eGFP-U104L-LacI-p72-LacO; and extracting a plasmid DNA;

(3) cell transfection and recombinant virus screening by transfecting the homologous recombinant transfer vector pUC-p72-eGFP-U104L-LacI-p72-LacO into swine bone marrow-derived macrophages (BMDMs) with a DNA transfection reagent, directly conducting ASFV infection 6 h after transfection, and picking a single infected fluorocyte; and (4) identification of the recombinant virus by conducting PCR identification with primers for the D1133L gene to determine whether the deletion is successful; adding IPTG, and conducting a Western Blot assay of a target gene to determine that an expression of the D1133L protein is inhibited in purified ASFV vD1133Li in the absence of the IPTG.

6. The method according to claim 5, wherein the left homologous arm has the nucleotide sequence set forth in SEQ ID NO: 6, and the right homologous arm has the nucleotide sequence set forth in SEQ ID NO: 7.

7. The method according to claim 5, wherein the p72-eGFP-U104L-LacI-p72-LacO screening expression cassette has the nucleotide sequence set forth in SEQ ID NO: 5.

8. The method according to claim 5, wherein the primers for the D1133L gene comprise D1133L-F: 5'-C A T G C A C T T C G G T G A AAAA C T-3' (SEQ ID NO:9), and D1133L-R: 5'-GAGAATACATAAGGGTTTGCGT-3' (SEQ ID NO:10).

\* \* \* \* \*

SEQUENCE LISTING

```
Sequence total quantity: 30
SEQ ID NO: 1              moltype = DNA  length = 213
FEATURE                   Location/Qualifiers
source                    1..213
                          mol_type = other DNA
                          note = Nucleotide sequence of p72-eGFP-SV40polyA
                          organism = synthetic construct
SEQUENCE: 1
gcagctgcag aagacagcaa cttcctgcat gacacccgcg aattcaccag cctagtgcca   60
gatgaggccg ataacaagcc agaggacgac gaggagtccg gggccaagcc aaagaagaag   120
aagcacctct tccccaagct gagcagccac aagagcaagt aaaaattgaa gcgaaaaaaa   180
gtagaaaaaa aaccggtctc ttggcccgga tcc                                213

SEQ ID NO: 2              moltype = DNA  length = 1019
FEATURE                   Location/Qualifiers
source                    1..1019
                          mol_type = other DNA
                          note = DNA sequence of a left homologous arm of D1133L gene
                          organism = African swine fever virus
SEQUENCE: 2
taaaaatcat gtcctatttt tctttgctca ataagcatcc aaatattttc atggcgtttt   60
attaattgtt cattattgaa cgtatcacaa agatcattta taaattgcag atagtttatt   120
atttctttca agagagtaac aaacattact tcagcagaac atataatagg taattcagtg   180
gcgttaaaag aattttgatc ttgttgatac gccaatggcg aggacttaag gagattttggg  240
ggtcttgccc aaaaccctag gctgctgttc ttgtttttta ggcgtcata aagaaatgaa   300
agcacattgc aaggcttaag ccgcgacatc tccttcccct tgggcccttt ccatatttt   360
agatctaaga tctcatccga gcttatagag taggtatagt aaagttttc aaaaaagcat   420
atctgcttga agtcttttt agaacgactt tcaagaagca tttctataat gttaacaagt   480
tttgttaggt ttaaggcctg ttcctgtgta agctcctctt gcacgtgata gactgaaaaa   540
gtgtgcttag gaatgaaaat actccccgtg gcactggcct gttgtctgcc aggtatatag   600
tacacgctgc tgttagcaag ctgtaccggc acaatttgcc ccacttctgc aacattattt   660
tgcgattcgg acgagggtat gacaatagtt acgggttcag tcaataggct ttcgccgaga   720
ataattactac tgtcattttt aatatttta acggccgcta ttaaatcaaa ggcatttaag   780
taagaaacaa cagcagaaaa tcttacatgc atatatcctc ttccgctatt attcgtacgc   840
ataataaaac aaggggagcg ttgtataacg ccagtaatat taagaataaa actgtttttg   900
aaacacttac ccacataaat gttttcaagc tccttcaaaa gatgagcctc cacatttgta   960
caaaaattgg taggatcatc aatattcaac gttgtctcaa aaatttttg gtcgatcat    1019

SEQ ID NO: 3              moltype = DNA  length = 1016
FEATURE                   Location/Qualifiers
source                    1..1016
                          mol_type = other DNA
                          note = DNA sequence of a right homologous arm of D1133L gene
                          organism = African swine fever virus
SEQUENCE: 3
ccatgattac gaattctatg tttattacaa tcgtgggatt tgcagcgcgc tgctcgacga   60
ttatatctaa aatattttt ttgcttaaaa cgggcttatc aacgattaaa attaattctt   120
```

-continued

```
cataatgttt tttttcatta agcgtattcg ttaaaagcgt tctcatgtcg cctccgtggt  180
gaacgtactt gccatttgct ccaaagataa acacggatac gattccgtga ttcagcgtct  240
ccgcgttaat acgaaaaaat cctgtattaa gtaccatttg aacaaactta tcatatggta  300
ccttttcttc aacagcacc atcttacgat attcaataaa ctcgtaaata tacgtaaata  360
actttgcat ggccataatt aattttgtgt tatattttat ttgagattaa tataactgtt  420
caattgtaat aaatggacac tgaaacgtct ccactgcttt ctcataacct gtcaacccgc  480
gagggaatta acaaagcac ccaaggcctt ttagcccata caatcgccaa atatcccgga  540
acaactgcga ttctcctggg cattttgatt ttgctcatta ttattcttat catcgttgcc  600
atcgttttact ataaccggac tattgactgc aagtcgagca tacctaaacc tcctcctagc  660
tactatgtac aacaacctga gcctcaccac catttcccgg tattctttag aaaaaggaaa  720
aactccacct ccctgcagtc ccacattcca agcgacgaac aattagctga acttgcgcat  780
tcataagata taatactttt tataaaaaag taagtataat atgagtttga tagtgattgc  840
ctgctgttta gtcttaatta tttatcttat tattattta tatccagaaa aaagaataa  900
cgcctcttcg ttagaaaaac aagttgatac gcttatttac agtattcata aaaaacaatt  960
gcaatacaga atcacataaa agttttcata aaaaggttta ttttttttat gataat    1016

SEQ ID NO: 4              moltype = DNA  length = 1000
FEATURE                   Location/Qualifiers
source                    1..1000
                          mol_type = other DNA
                          note = Nucleotide sequence of the complete D1133L gene
                          organism = African swine fever virus
SEQUENCE: 4
atggcgtatc ccgaattgga tgccgcagac ttttgcagc agttggcgcg aagaaaggag   60
tttaaatcgt tgatttcccc tcctgtcgac caaaaagagc tcattcgtga tctgcgggct  120
cattttgtcc agatcggtgg gcctggctgc gagaaggggg ggcgagcgtt ttttccgtgt  180
gaccccatcg cgtcgccctt tccttccatc aaggggtctcc aattgcataa tgcccagctt  240
ttcgtccaaa actttcaaaa tcccaacacg ccctactcgc gtcttttatt aaactggcag  300
accgggacgg gaaaaagcat tgccgcgatt gccatcgcgc gtcaatttat gaaccactac  360
atgaattta ttgaaaatgc gccctggatt tttgtggtag cttttacacg cgccatcatt  420
caaacagaaa tgctaagacg tcctgagctg ggatttgttt cttacaagga ggtcgctgag  480
ctacaccggc ttcttcacat tgcaagcag tctggcagca ccacgtcggt cgaatcacgg  540
catctaaatg ggttcgttag tacgttaaag cgccgtttaa ccgatagaaa ccgcggaggc  600
tttttttcag tttacggcta taaggaattt gcatccaagc ttttcaatat tacgagtaag  660
ggtgaagaga aaaactttga tgtgctttct ctgtttcatc gttctgacga agcagaagat  720
acattgaatg agaacgatat atctcagttc gtgcaaaaa ttagcgaggc cgagacaaac  780
ggcctcatcc gggtgaatca aaaaatcatg gagcaactta ggggaggact gctcattgcg  840
gatgaaatac acacgtgta caatatccag gaacgaaata attatggcat cgcttttcag  900
tatgtcctgg atgccttcc acctcaccag gccccaggg ccgtcttcat gtcggcaacg  960
cccgtaaccg ggagtgtcat ggaatacgtc gacctgttaa                       1000

SEQ ID NO: 5              moltype = DNA  length = 3412
FEATURE                   Location/Qualifiers
source                    1..3412
                          mol_type = other DNA
                          note = DNA sequence of p72-eGFP-U104L-LacI-p72-LacO
                          organism = synthetic construct
SEQUENCE: 5
ttttaagctg atcgttaatt aattttttggt ttaactcttt gttattatca agatccttcg   60
cataaaccgc catatttaat aaaaacaata aattattttt ataacattat atatccggat  120
ggtgagcaag ggcgaggagc tgttcaccgg ggtggtgccc atcctggtcg agctggacgg  180
cgacgtaaac ggccacaagt tcagcgtgtc cggcgagggc gagggcgatg ccacctacgg  240
caagctgacc ctgaagttca tctgcaccac cggcaagctg cccgtgccct ggcccaccct  300
cgtgaccacc ctgacctacg gcgtgcagtg cttcagccgc taccccgacc acatgaagca  360
gcacgacttc ttcaagtccg ccatgcccga aggctacgtc caggagcgca ccatcttctt  420
caaggacgac ggcaactaca agacccgcgc cgaggtgaag ttcgagggcg acacccttggt  480
gaaccgcatc gagctgaagg gcatcgactt caaggaggac ggcaacatcc tggggcacaa  540
gctggagtac aactacaaca gccacaacgt ctatatcatg gccgacaagc agaagaacgg  600
catcaaggtg aacttcaaga tccgccacaa catcgaggac ggcagcgtgc agctcgtgga  660
ccactaccag cagaacaccc ccatcggcga cggccccgtg ctgctgcccg acaaccacta  720
cctgagcacc cagtccgccc tgagcaaaga ccccaacgag aagcgcgatc acatggtcct  780
gctggagttc gtgaccgccg ccgggatcac tctcggcatg gacgagctgt acaagtaagt  840
ccccggggac aaaaaaaaaa ctcgatcgac ctcgatggta cccgtcgacg gcttttaatt  900
agatttgtga aaatttttt ccagatctat aaaaaggct tttttttcca aatttaaca   960
tgttttttcg taatataaca ctacacttaa gatgaaacca gtaacgttat acgatgtcgc  1020
agagtatgcc ggtgtctctt atcagaccgt ttcccgcgtg gtgaaccagg ccagccacgt  1080
ttctgcgaaa acgcgggaaa agtggaagc ggcgatggcg gagctgaatt acattcccaa  1140
ccgcgtggca caactggcgg gcaaacagtc gttgctgatt ggcgttgcca cctccag    1200
tctggccctc cacgcgtcgt cgcaaattgt cgcggcgatt aaatctcgcg ccgatcaagt  1260
gggtgccagc gtggtggtgt cgatggtaga acgaagcggc gtcgaagcct gtaaagcggc  1320
ggtgcacaat cttctcgcgc aacgcgtcag tgggctgatc attaactatc cgctggatga  1380
ccaggatgcc attgctgtgg aagctgcctg cactaatgtt ccggcgttat tcttgatgt  1440
ctctgaccag acacccatca acagtattat tttctcccat gaagacggta cgcgactggg  1500
cgtggagcat ctggtcgcat tgggtcacca gcaaatcgcg ctgttagcgg cccattaag  1560
ttctgtctcg gcgcgtctgc gtctggctgg ctggcataaa tatctcactc gcaatcaaat  1620
tcagccgata gcggaacggg aaggcgactg gagtgccatg tccggttttc aacaaaccat  1680
gcaaatgctg aatgagggca tcgttcccac tgcgatgctg gttgccaacg atcagatggc  1740
gctgggcgca atgcgcgcca ttaccgagtc cgggctgcgc gttggtgcgg atatttcggt  1800
agtgggatac gacgataccg aagacagctc atgttatatc ccgccgttaa ccaccatcaa  1860
```

```
acaggattt  cgcctgctgg  ggcaaaccag  cgtggaccgc  ttgctgcaac  tctctcaggg  1920
ccaggcggtg  aagggcaatc  agctgttgcc  cgtctcactg  gtgaaaagaa  aaaccaccct  1980
ggcgcccaat  acgcaaaccg  cctctccccg  cgcgttggcc  gattcattaa  tgcagctggc  2040
acgacaggtt  tcccgactgg  aaagcgggca  gtgagtcgag  gggatccact  agattcgaca  2100
aaaaaaaaac  tcgaccttca  gctcgacctg  caggcatgcc  gtacgggtga  tctgggtcgc  2160
cggaggaaaa  gtcaaaaggg  gcaggtagtt  catacaccaa  aaagtttttt  ttttctgcca  2220
gcaagagcgt  gtcaataatt  ttaagctgat  cgttaattaa  ttttttggttt  aactctttgt  2280
tattatcaag  atccttcgca  taaaccgcca  tatttaataa  aaacaataaa  ttattttat   2340
aacattatat  atctagaaat  tgtgagcgga  taacaattgc  ctaggtcact  taggctagc   2400
gtatggcgta  tcccgaattg  gatgccgcag  acttttttgca  gcagttggcg  cgaagaaagg  2460
agtttaaatc  gttgatttcc  cctcctgtcg  accaaaaaga  gctcattcgt  gatctgcggg  2520
ctcatttttgt  ccagatcggt  gggcctggct  gcgagaaggg  ggggcgagcg  ttttttccgt  2580
gtgacccta   cgcgtcgccc  ttccttcca  tcaagggtct  ccaattgcat  aatgcccagc  2640
ttttcgtcca  aaactttcaa  aatcccaaca  cgccctactc  gcgtcttta  ttaaactggc  2700
agaccgggac  gggaaaaagc  attgccgcga  ttgccatcgc  gcgtcaattt  atgaaccact  2760
acatgaattt  tattgaaaat  gcgccctgga  ttttgtggt  aggctttaca  cgcgccatca  2820
ttcaaacaga  aatgctaaga  cgtcctgagc  tgggatttgt  ttcttacaag  gaggtcgctg  2880
agctacaccg  gcttcttcac  attgcaaagc  agtctggcag  caccacgtcg  gtcgaatcac  2940
ggcatctaaa  tgggttcgtt  agtacgttaa  agcgccgttt  aaccgataga  aaccgcggag  3000
gcttttttca  gttttacggc  tataaggaat  ttgcatccaa  gcttttcaat  attacgagta  3060
agggtgaaga  gaaaaacttt  gatgtgcttt  ctctgtttca  tcgttctgac  gaagcagaag  3120
atacattgaa  tgagaacgat  atatctcagt  tcgtgcagaa  aattagcgag  gccgagacaa  3180
acggcctcat  ccgggtgaat  caaaaaatca  tggagcaact  taggggagga  ctgctcattg  3240
cggatgaaat  acacaacgtg  tacaatatcc  aggaacgaaa  taattatggc  atcgctttac  3300
agtatgtcct  ggatgccttt  ccacctcacc  aggcccccag  ggccgtcttc  atgtcggcaa  3360
cgcccgtaac  cgggagtgtc  atggaatacg  tcgacctgtt  aaaagcttgg  ca          3412
```

SEQ ID NO: 6                moltype = DNA   length = 1001
FEATURE                     Location/Qualifiers
source                      1..1001
                            mol_type = other DNA
                            note = DNA sequence of a left recombinant homologous arm of
                             D117L gene
                            organism = African swine fever virus
SEQUENCE: 6

```
gcctaggtca  cttaggctag  ccgtatggcg  tatcccgaat  tggatgccgc  agactttttg   60
cagcagttgg  cgcgaagaaa  ggagtttaaa  tcgttgattt  cccctcctgt  cgaccaaaaa  120
gagctcattc  gtgatctgcg  ggctcatttt  gtccagatcg  gtgggcctgg  ctgcgagaag  180
gggggcgag  cgttttttcc  gtgtgacccc  tacgcgtcgc  ccttccttc   catcaaggg   240
ctccaattgc  ataatgccca  gcttttcgtc  caaaactttc  aaaatcccaa  cacgccctac  300
tcgcgtcttt  tattaaactg  gcagaccggg  acgggaaaaa  gcattgccgc  gattgccatc  360
gcgcgtcaat  ttatgaacca  ctacatgaat  tttattgaaa  atgcgccctg  gattttttgtg  420
gtaggcttta  cacgcgccat  cattcaaaca  gaaatgctaa  gacgtcctga  gctgggattt  480
gtttcttaca  aggaggtcgc  tgagctacac  cggcttcttc  acattgcaaa  gcagtctggc  540
agcaccacgt  cggtcgaatc  acggcatcta  aatgggttcg  ttagtacgtt  aaagcgccgt  600
ttaaccgata  gaaaccgcgg  aggctttttt  cagttttacg  gctataagga  atttgcatcc  660
aagcttttca  atattacgag  taagggtgaa  gagaaaaact  ttgatgtgct  ttctctgttt  720
catcgttctg  acgaagcaga  agatacattg  aatgagaacg  atatatctca  gttcgtgcaa  780
aaaattagcg  aggccgagac  aaacggcctc  atccgggtga  atcaaaaaat  catggagcaa  840
cttaggggag  gactgctcat  tgcggatgaa  atacacaacg  tgtacaatat  ccaggaacga  900
aataattatg  gcatcgcttt  acagtatgtc  ctggatgcct  ttccacctca  ccaggccccc  960
agggccgtct  tcatgtcggc  aacgcccgta  accgggagtg  t                      1001
```

SEQ ID NO: 7                moltype = DNA   length = 1016
FEATURE                     Location/Qualifiers
source                      1..1016
                            mol_type = other DNA
                            note = DNA sequence of a right recombinant homologous arm
                             of D117L gene
                            organism = African swine fever virus
SEQUENCE: 7

```
ccatgattac  gaattctatg  tttattacaa  tcgtgggatt  tgcagcgcgc  tgctcgacga   60
ttatatctaa  aatattttt   ttgcttaaaa  cgggcttatc  aacgattaaa  attaattctt  120
cataatgttt  tttttcatta  agcgtattcg  ttaaaagcgt  tctcatgtcg  cctccgtgt   180
gaacgtactt  gccatttgct  ccaaagataa  acacgatac   gattccgtga  ttcagcgtct  240
ccgcgttaat  acgaaaaaat  cctgtattaa  gtaccatttg  aacaaactta  tcatatggta  300
ccttttcttc  caacagcacc  atcttacgat  attcaataaa  ctcgtaaata  tacgtaaata  360
acttttgcat  ggccataatt  aattttgtgt  tatattttat  ttgagattaa  tataactgtt  420
caattgtaat  aaatggacac  tgaaacgtct  ccactgcttt  ctctaaacct  gtcaaccccgc  480
gagggaatta  aacaaagcac  ccaaggcctt  ttagcccata  caatcgccaa  atatcccgga  540
acaactgcga  ttctcctggg  cattttgatt  ttgctcatta  ttattcttat  catcgttgcc  600
atcgtttact  ataaccggac  tattgactgc  aagtcgagca  tacctaaacc  tcctcctagc  660
tactatgtac  aacaacctga  gcctcaccac  catttcccgg  tattctttag  aaaaaggaaa  720
aactccacct  ccctgcagtc  ccaattcca   agcgacgaac  attagctga   acttgcgcat  780
tcataagata  taatactttt  tataaaaag   taagtataat  atgagtttga  tagtgattgc  840
ctgctgttta  gtcttaatta  ttatacttat  tattattttta  tatccagaaa  aaagaataa   900
cgcctcttcg  ttagaaaaac  aagttgatac  gcttatttac  agtattcata  aaaaacaatt  960
gcaatacaga  atcacataaa  agttttcata  aaaggttta  tttttttttat  gataat      1016
```

```
SEQ ID NO: 8           moltype = DNA  length = 21
FEATURE                Location/Qualifiers
source                 1..21
                       mol_type = other DNA
                       note = Primer D1133L-F
                       organism = synthetic construct
SEQUENCE: 8
catgcacttc ggtgaaaaac t                                                   21

SEQ ID NO: 9           moltype = DNA  length = 22
FEATURE                Location/Qualifiers
source                 1..22
                       mol_type = other DNA
                       note = Primer D1133L-R
                       organism = synthetic construct
SEQUENCE: 9
gagaatacat aagggtttgc gt                                                  22

SEQ ID NO: 10          moltype = DNA  length = 22
FEATURE                Location/Qualifiers
source                 1..22
                       mol_type = other DNA
                       note = Primer hISG56-F
                       organism = synthetic construct
SEQUENCE: 10
cttgagcatc ctcgggttca tc                                                  22

SEQ ID NO: 11          moltype = DNA  length = 22
FEATURE                Location/Qualifiers
source                 1..22
                       mol_type = other DNA
                       note = Primer hISG56-R
                       organism = synthetic construct
SEQUENCE: 11
aagtcagcag ccaggtttag gg                                                  22

SEQ ID NO: 12          moltype = DNA  length = 19
FEATURE                Location/Qualifiers
source                 1..19
                       mol_type = other DNA
                       note = Primer hISG15-F
                       organism = synthetic construct
SEQUENCE: 12
tggacaaatg cgacgaacc                                                      19

SEQ ID NO: 13          moltype = DNA  length = 18
FEATURE                Location/Qualifiers
source                 1..18
                       mol_type = other DNA
                       note = Primer hISG15-R
                       organism = synthetic construct
SEQUENCE: 13
cccgctcact tgctgctt                                                       18

SEQ ID NO: 14          moltype = DNA  length = 21
FEATURE                Location/Qualifiers
source                 1..21
                       mol_type = other DNA
                       note = Primer hIFN-beta-F
                       organism = synthetic construct
SEQUENCE: 14
gacatccctg aggagattaa g                                                   21

SEQ ID NO: 15          moltype = DNA  length = 21
FEATURE                Location/Qualifiers
source                 1..21
                       mol_type = other DNA
                       note = Primer hIFN-beta-R
                       organism = synthetic construct
SEQUENCE: 15
atgttctgga gcatctcata g                                                   21

SEQ ID NO: 16          moltype = DNA  length = 21
FEATURE                Location/Qualifiers
source                 1..21
                       mol_type = other DNA
                       note = Primer hGAPDH-F
                       organism = synthetic construct
SEQUENCE: 16
```

```
cgggaagctt gtgatcaatg g                                                  21

SEQ ID NO: 17           moltype = DNA   length = 20
FEATURE                 Location/Qualifiers
source                  1..20
                        mol_type = other DNA
                        note = Primer hGAPDH-R
                        organism = synthetic construct
SEQUENCE: 17
ggcagtgatg gcatggactg                                                    20

SEQ ID NO: 18           moltype = DNA   length = 23
FEATURE                 Location/Qualifiers
source                  1..23
                        mol_type = other DNA
                        note = Primer LP3056-130endoSur-F
                        organism = synthetic construct
SEQUENCE: 18
gtgattgcct gctgtttagt ctt                                                23

SEQ ID NO: 19           moltype = DNA   length = 23
FEATURE                 Location/Qualifiers
source                  1..23
                        mol_type = other DNA
                        note = Primer LP3057-130endoSur-R
                        organism = synthetic construct
SEQUENCE: 19
caggacgtct tagcatttct gtt                                                23

SEQ ID NO: 20           moltype = DNA   length = 20
FEATURE                 Location/Qualifiers
source                  1..20
                        mol_type = other DNA
                        note = Primer LP2918/LP3057
                        organism = synthetic construct
SEQUENCE: 20
gacctgcagg catgccgtac                                                    20

SEQ ID NO: 21           moltype = DNA   length = 20
FEATURE                 Location/Qualifiers
source                  1..20
                        mol_type = other DNA
                        note = RT-qPCR primer D1133L-F
                        organism = synthetic construct
SEQUENCE: 21
cttctggaaa acggggtaca                                                    20

SEQ ID NO: 22           moltype = DNA   length = 20
FEATURE                 Location/Qualifiers
source                  1..20
                        mol_type = other DNA
                        note = RT-qPCR primer D1133L-R
                        organism = synthetic construct
SEQUENCE: 22
caagataaga accccccgaca                                                   20

SEQ ID NO: 23           moltype = DNA   length = 20
FEATURE                 Location/Qualifiers
source                  1..20
                        mol_type = other DNA
                        note = RT-qPCR primer beta-actin-human-F
                        organism = synthetic construct
SEQUENCE: 23
agagctacga gctgcctgac                                                    20

SEQ ID NO: 24           moltype = DNA   length = 20
FEATURE                 Location/Qualifiers
source                  1..20
                        mol_type = other DNA
                        note = RT-qPCR primer beta-actin-human -R
                        organism = synthetic construct
SEQUENCE: 24
agcactgtgt tggcgtacag                                                    20

SEQ ID NO: 25           moltype = DNA   length = 22
FEATURE                 Location/Qualifiers
source                  1..22
                        mol_type = other DNA
                        note = RT-qPCR primer GAPDH-F (M)
```

```
                    organism = synthetic construct
SEQUENCE: 25
catgttccag tatgactcca ct                                                    22

SEQ ID NO: 26       moltype = DNA  length = 22
FEATURE             Location/Qualifiers
source              1..22
                    mol_type = other DNA
                    note = RT-qPCR primer GAPDH-R (M)
                    organism = synthetic construct
SEQUENCE: 26
gtagactcca cgacatactc ag                                                    22

SEQ ID NO: 27       moltype = DNA  length = 20
FEATURE             Location/Qualifiers
source              1..20
                    mol_type = other DNA
                    note = RT-qPCR primer p30-F
                    organism = synthetic construct
SEQUENCE: 27
ctccgatgag ggctcttgct                                                       20

SEQ ID NO: 28       moltype = DNA  length = 22
FEATURE             Location/Qualifiers
source              1..22
                    mol_type = other DNA
                    note = RT-qPCR primer p30-R
                    organism = synthetic construct
SEQUENCE: 28
agacggaatc ctcagcatct tc                                                    22

SEQ ID NO: 29       moltype = DNA  length = 18
FEATURE             Location/Qualifiers
source              1..18
                    mol_type = other DNA
                    note = RT-qPCR primer p72-F
                    organism = synthetic construct
SEQUENCE: 29
tgcgatgatg attacctt                                                         18

SEQ ID NO: 30       moltype = DNA  length = 19
FEATURE             Location/Qualifiers
source              1..19
                    mol_type = other DNA
                    note = RT-qPCR primer p72-R
                    organism = synthetic construct
SEQUENCE: 30
attctcttgc tctggatac                                                        19
```